United States Patent
Jenni

(10) Patent No.: US 10,492,933 B2
(45) Date of Patent: Dec. 3, 2019

(54) STENT AND KIT OF STENTS FOR ADJUSTABLE INTERVENTIONAL REDUCTION OF BLOOD FLOW

(71) Applicant: IntelliStent AG, Hergiswil (CH)

(72) Inventor: Rolf Jenni, Zürich (CH)

(73) Assignee: INTELLISTENT AG, Hergiswil (CH)

( * ) Notice: Subject to any disclaimer, the term of this patent is extended or adjusted under 35 U.S.C. 154(b) by 98 days.

(21) Appl. No.: 15/537,059

(22) PCT Filed: Dec. 8, 2015

(86) PCT No.: PCT/EP2015/078937
§ 371 (c)(1),
(2) Date: Jun. 16, 2017

(87) PCT Pub. No.: WO2016/096529
PCT Pub. Date: Jun. 23, 2016

(65) Prior Publication Data
US 2017/0367855 A1 Dec. 28, 2017

(30) Foreign Application Priority Data

Dec. 18, 2014 (CH) ........................ 1972/14

(51) Int. Cl.
*A61F 2/90* (2013.01)
*A61F 2/852* (2013.01)
(Continued)

(52) U.S. Cl.
CPC ........ *A61F 2/852* (2013.01); *A61B 17/12036* (2013.01); *A61B 17/12109* (2013.01);
(Continued)

(58) Field of Classification Search
CPC ...................................................... A61F 2/06
(Continued)

(56) References Cited

U.S. PATENT DOCUMENTS

| 5,618,301 A | 4/1997 | Hauenstein et al. |
| 5,980,564 A * | 11/1999 | Stinson .................... A61F 2/90 606/191 |

(Continued)

FOREIGN PATENT DOCUMENTS

| DE | 4101937 A1 | 7/1992 |
| EP | 0647438 A1 | 4/1995 |

(Continued)

OTHER PUBLICATIONS

Gillum RF. Epidemiology of congenital heart disease in the United States. Am HeartJ 1994; 127:919-27.

(Continued)

*Primary Examiner* — Suzette J Gherbi
(74) *Attorney, Agent, or Firm* — Paul D. Bianco; Gary S. Winer; Fleit Intellectual Property Law

(57) ABSTRACT

A kit of stents and an adjustable multi-lumen stent for adjustable interventional reduction of blood flow in a blood vessel. The kit includes: a first reduction stent having in an expanded conformation at least one widened section and a narrowed section, the narrowed section defining a central lumen providing reduced fluid communication between an upstream end and a downstream end of the first reduction stent; at least one expandable dilatation stent having a tubular form insertable into and expandable in the central lumen of the first reduction stent to define an enlarged central lumen; at least one second reduction stent having a narrowed tubular section insertable into the central lumen of the first reduction stent or the central lumen of the dilatation stent to define an reduced central lumen, and having an anchoring element at its upstream end.

20 Claims, 6 Drawing Sheets

(51) Int. Cl.
*A61F 2/07* (2013.01)
*A61B 17/12* (2006.01)
*A61F 2/82* (2013.01)
*A61B 17/00* (2006.01)
*A61F 2/06* (2013.01)
*A61F 2/848* (2013.01)

(52) U.S. Cl.
CPC .. *A61B 17/12136* (2013.01); *A61B 17/12172* (2013.01); *A61F 2/07* (2013.01); *A61F 2/82* (2013.01); *A61F 2/90* (2013.01); *A61B 2017/00867* (2013.01); *A61F 2002/068* (2013.01); *A61F 2002/8486* (2013.01); *A61F 2210/0014* (2013.01); *A61F 2210/0076* (2013.01); *A61F 2230/001* (2013.01); *A61F 2250/001* (2013.01); *A61F 2250/0039* (2013.01); *A61F 2250/0062* (2013.01); *A61F 2250/0063* (2013.01); *A61F 2250/0064* (2013.01)

(58) Field of Classification Search
USPC .................................. 623/1.15–1.36
See application file for complete search history.

(56) References Cited

U.S. PATENT DOCUMENTS

| | | | | |
|---|---|---|---|---|
| 6,004,348 | A * | 12/1999 | Banas | A61F 2/07 606/198 |
| 6,120,534 | A | 9/2000 | Ruiz | |
| 6,436,132 | B1 * | 8/2002 | Patel | A61F 2/07 623/1.13 |
| 6,547,814 | B2 * | 4/2003 | Edwin | A61F 2/07 623/1.13 |
| 9,597,204 | B2 * | 3/2017 | Benary | A61F 2/07 |
| 2003/0078647 | A1 * | 4/2003 | Vallana | A61F 2/82 623/1.11 |
| 2006/0058833 | A1 | 3/2006 | VanCamp et al. | |
| 2006/0265049 | A1 * | 11/2006 | Gray | A61F 2/91 623/1.16 |
| 2008/0243224 | A1 * | 10/2008 | Wallace | A61B 17/12118 623/1.11 |
| 2009/0036977 | A1 * | 2/2009 | Rassat | A61F 2/07 623/1.42 |
| 2009/0187238 | A1 * | 7/2009 | Weber | A61F 2/95 623/1.12 |
| 2010/0023046 | A1 | 1/2010 | Heidner et al. | |
| 2010/0286758 | A1 | 11/2010 | Berglund | |
| 2010/0292780 | A1 * | 11/2010 | Straubinger | A61F 2/2427 623/1.23 |
| 2012/0010690 | A1 * | 1/2012 | Richter | A61F 2/86 623/1.2 |
| 2013/0073026 | A1 * | 3/2013 | Russo | A61F 2/852 623/1.12 |
| 2013/0096580 | A1 | 4/2013 | Cohn et al. | |
| 2013/0150950 | A1 * | 6/2013 | Schlick | A61F 2/07 623/1.16 |
| 2014/0180392 | A1 * | 6/2014 | Shoham | A61F 2/852 623/1.15 |
| 2014/0371836 | A1 * | 12/2014 | Silveira | A61F 2/07 623/1.2 |
| 2015/0088239 | A1 | 3/2015 | Ben-Muvhar et al. | |
| 2015/0105850 | A1 * | 4/2015 | Shahriari | A61F 2/856 623/1.13 |
| 2017/0049589 | A1 * | 2/2017 | Han | A61L 27/34 |

FOREIGN PATENT DOCUMENTS

| | | |
|---|---|---|
| EP | 1276437 A2 | 1/2003 |
| WO | 2001/072239 A2 | 10/2001 |
| WO | 03028522 A2 | 4/2003 |
| WO | 2003/074119 A1 | 9/2003 |
| WO | 03074119 A1 | 9/2003 |
| WO | 2004/014257 A1 | 2/2004 |
| WO | 2009/105699 A1 | 8/2009 |
| WO | 2009105699 A1 | 8/2009 |
| WO | 2010114585 A1 | 10/2010 |

OTHER PUBLICATIONS

Hoffman J1, Kaplan S. The incidence of congenital heart disease. J Am Coli Cardiol2002;39: 1890-900.
Marelli AJ, Mackie AS, 1onescu-Ittu R, Rahme E, Pilote L. Congenital heart disease in the general population: changing prevalence and age distribution. Circulation 2007; 15:163-72.
Jonas RA. Congenital heart surgery in developing countries. Semin Thorac Cardiovasc Surg Pediatr Card Surg Annu 2008: 3-6.
Bernier PL, Stefanescu A, Samoukovic G, Tchervenkov CI. The challenge of congenital heart disease worldwide: epidemiologic and demographic facts. Semin Tho rae Cardiovasc Surg PediatrCard SurgAnnu 2010; 13: 26-34.
Neirotti R. Paediatric cardiac surgery in less privileged parts of the world. Cardiol Young 2004; 14: 341-6.
Yacoub MH. Establishing pediatric cardiovascular services in the developing world: a wake-up call. Circulation 2007; 116: 1876-8.
Tchervenkov CI, Jacobs JP, Bernier PL, et al. The improvement of care for paediatric and congenital cardiac disease across the World: a challenge for the World Society for Pediatric and Congenital Heart Surgery. Cardiol Young 2008; 18 Suppl2:63-9.
Zheleva B. Linked by a common purpose: Global Efforts for Improving Pediatric Heart Health: A Report by Children's Heart Link. Congenital Cardiology Today 2007;5: 1-15.
Mocumbi AD, Lameira E, Yaksh A, Paul L, Ferreira MB, Sidi D. Challenges on the management of congenital heart disease in developing countries. Int J Cardiol 2011;148:285-8.
Trucco SM, Barnoya], Larrazabal LA, Castaneda A, Teitel DF. Detection rates of congenital heart disease in Guatemala Cardiol Young 2011; 21: 15360.23.
Shah GS, Singh MK, Pandey TR, Kalakheti BK, Bhandari GP. Incidence of congenital heart disease in tertiary care hospital. Kathmandu Univ Med J (KUMJ) 2008;6: 33-6.
Wickramasinghe P, Lamabadusuriya SP, Narenthiran S. Prospective study of congenital heart disease in children. Ceylon Med J 2001;46:96-8.
Samanek M, Slavik Z, Zborilova B, Hrobonova V, Voriskova M, Skovranek J. Prevalence, treatment, and outcome of heart disease in live-born children: a prospective analysis of 91 ,823 live-born children. Pediatr Cardiol 1989; 10:205-11.
Saxena A. Congenital heart disease in India: a status report. Indian J Pediatr 2005;72:595-8.
Rao SG. Pediatric cardiac surgery in developing countries. Pediatr Cardiol 2007; 28: 144-8.
Guitti Jc. Epidemiological characteristics of congenital heart diseases in Londrina, Parana south Brazil. Arq Bras Cardiol 2000;74: 395-404.
Penny DJ, Vick GW, 3rd. Ventricular septal defect. Lancet 2011; 377: 1103-12.
Beghetti M, Galie N. Eisenmenger syndrome a clinical perspective in a new therapeutic era of pulmonary arterial hypertension. J Am Coil Cardiol 2009;53:733-40.
Pinho P, Von Oppell UO, Brink J, Hewitson J. Pulmonary artery banding: adequacy and long-term outcome. Eur J Cardiothorac Surg 1997; 11: 105-11.
Schranz D, Rupp 5, Muller M, et al. Pulmonary artery banding in infants and young children with left ventricular dilated cardiomyopathy: A novel therapeutic strategy before heart transplantation. J Heart Lung Transplant 2013; 32:475-481.
English translation of International Preliminary Report on Patentability dated Jun. 20, 2017 for International Application No. PCT/EP2015/078937.
International Search Report dated Mar. 16, 2016 for International Application No. PCT/EP2015/078937 filed Dec. 8, 2015.
Written Opinion dated Jun. 23, 2016 for International Application No. PCT/EP2015/078937 filed Dec. 8, 2015.

(56) References Cited

OTHER PUBLICATIONS

Chinese Search Report for Chinese Patent Application No. 2015800696364, dated Feb. 22, 2019.
Office Action for Chinese Patent Application No. 2015800696364, dated Mar. 4, 2019.

* cited by examiner

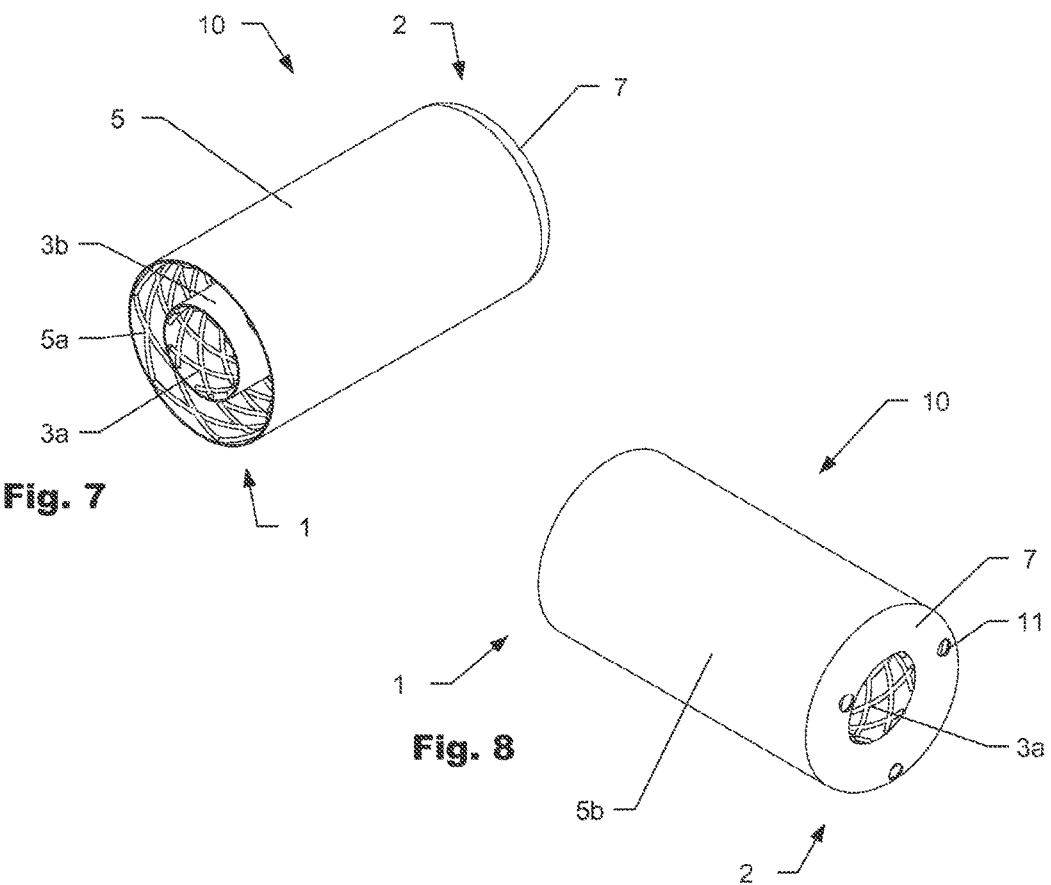
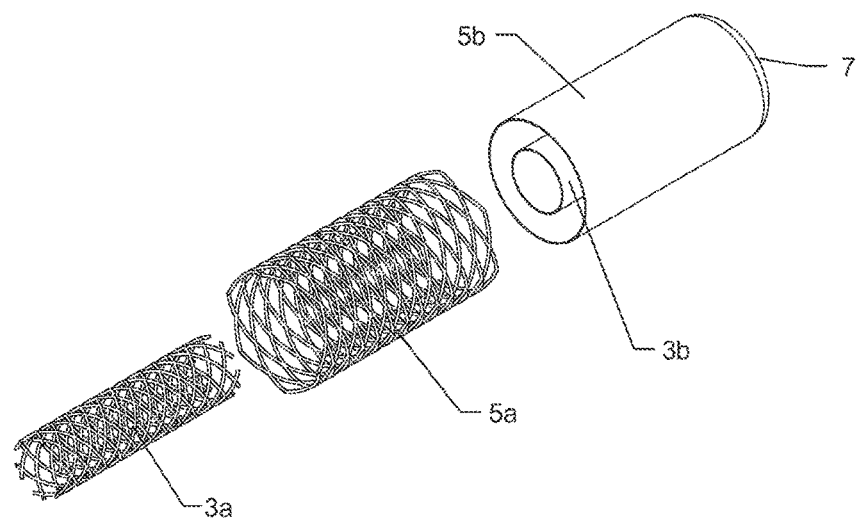
Fig. 9

STENT AND KIT OF STENTS FOR ADJUSTABLE INTERVENTIONAL REDUCTION OF BLOOD FLOW

TECHNICAL FIELD

The invention relates to a stent or a kit of stents for interventional reduction of blood flow. In particular a covered pulmonary stent for interventional reduction of pulmonary artery blood flow in patients to avoid the development of pulmonary artery hypertension and in patients with pulmonary hypertension and established Eisenmenger's syndrome associated with uncorrected heart disease.

PRIOR ART

Eisenmenger's syndrome is a systemic disease involving multiple organ systems caused by longstanding congenital cardiac defects which cause a high pulmonary artery blood pressure with reduced pulmonary blood flow, decreased oxygen uptake and decreased oxygen saturation of the arterial blood resulting in the so-called "blue babies" or "blue children". Eisenmenger's syndrome is characterized by multiple clinical features such as cyanosis with its typical blue tinge to the skin, swollen or clubbed finger tips, fainting or syncope, heart failure, arrhythmia or irregular heart rhythms, bleeding disorders, coughing up blood, iron deficiency, kidney problems, stroke, gout and gallstones. Eisenmenger patients do not grow normally, have a dramatically decreased quality of life and severely limited physical capacity, all associated with a markedly decreased life expectancy. In other words, they have just too much to die, but too little to have an acceptable life.

Congenital heart disease is the most common form of birth defects, occurring in about 1% of life births (Ref 1-4, see below). Nowadays, the majority of children born with congenital heart disease, if repaired in time, are expected to lead normal lives. The privilege of early diagnosis and timely surgical management is mostly restricted to children living in developed countries. However, the majority of children born with congenital heart disease live in developing countries without access to timely treatment; hence, about 90% of all children born yearly with congenital heart defects around the world receive suboptimal care (Ref 6, Ref 8).

Many countries with populations between 15 and 70 million people are without a single specialized paediatric heart centre (Ref 7). In Africa, on average, there is only one centre capable to perform open-heart surgery and advanced cardiac care per 33 million peoples compared to one centre per 1 million peoples in the Western world, and even fewer centres will have the capacity to treat children with congenital heart disease (Ref 6, 9).

Therefore, in these countries, the majority of children born with congenital heart disease does not have access to specialized surgical treatment and are often diagnosed late (Ref 10). Furthermore, a substantial number of children with severe forms of heart defects will not be diagnosed at all (Ref 10, Ref 11). Hence, the mortality of children with congenital heart disease living in developing countries is considerably higher compared to those living in the Western world (Ref 5). Indeed, mortality rates up to 75% have been reported (Ref 5, Ref 12-14) and it has been assumed that in the developing world millions of children die or suffer serious consequences from their cardiac malformations which could effectively be prevented (Ref 7, Ref 9). The sobering fact is that most children die while waiting for surgery. For instance in India, approximately 1-2 millions of children with congenital heart disease is awaiting surgery (Ref 15, Ref 16).

Excessive pulmonary blood flow and consecutive pulmonary hypertension is observed in congenital heart defects with left-to-right shunts such as large ventricular or atrial septal defects, which are among the most frequently observed congenital heart diseases (Ref 13, Ref 17, Ref 18).

Under these circumstances, fixed secondary pulmonary hypertension develops within years finally resulting in Eisenmenger's syndrome (Ref 18, Ref 19). Pulmonary artery banding has frequently been performed as an interim palliative procedure to reduce increased pulmonary blood flow and to protect the pulmonary vasculature from hypertrophy and consecutive irreversible pulmonary hypertension (Ref 19, Ref 20). However, surgical pulmonary artery banding (the Battista operation) is not feasible in many developing countries as open heart surgery is often not available, technically demanding, and expensive. Moreover, the majority of patients with congenital heart disease resulting in fixed pulmonary artery hypertension have become inoperable and this is also true in highly developed countries where latest technologies are available. In fact, established Eisenmenger's syndrome represents an inoperable, devastating disease with limited palliative treatment options resulting in markedly reduced quality of life as well as reduced life expectancy. In addition, life-long palliative treatment of Eisenmenger's syndrom is only possible with a multidisciplinary approach resulting in extremely high costs of treatment.

Placement of reductional stent into the main pulmonary artery would reduce pulmonary blood flow as well as the development Eisenmenger syndrome. Moreover, such a stent could replace surgical pulmonary artery banding and allow treating fully developed established Eisenmenger's syndrome by interventional technique. With this techniques, patients previously thought to be inoperable for live, could undergo definite surgical correction of the underlying heart disease, once the Eisenmenger syndrome has been reversed by such a stent.

Reduction of pulmonary artery pressure over a period of six to 12 months is known to normalize pulmonary artery pressure allowing secondary curative surgical treatment of congenital heart defects, which, as mentioned above, have become inoperable according to the current knowledge. This concept of primary reduction of pulmonary artery blood flow followed by definitive surgical correction of the underlying heart defect has already been proven by surgical pulmonary artery banding via median sternotomy, known as Battista operation for Eisenmenger's syndrome. However, surgical pulmonary artery banding is associated with a considerable operative mortality because of a highly unstable early postoperative course necessitating sophisticated postoperative intensive care treatment which is far less developed than surgery in developing contrast or even completely absent. For these reasons, the Battista procedure has only been carried out in less than 50 patients with very few undergoing total correction of the underlying heart disease in a second stage procedure. Nevertheless, the concept of primary banding of the pulmonary artery with a subsequent decrease of the chronically high pulmonary artery pressure to normal values followed by total correction of the underling heart defect is proven.

In contrast to surgical pulmonary artery banding, interventional treatment of Eisenmenger syndrome by stenting could easily be implemented in developing countries, as it is a simple procedure performed in local anaesthesia without need for cardiopulmonary bypass or post-interventional intensive care.

The insertion of a pulmonary artery reductional stent would prevent the development of severe pulmonary artery hypertension and would even be able to completely reverse fully developed Eisenmenger's syndrome allowing complete surgical correction of the underlying cardiac malformation. Anatomical correction normalizes growth of the patient, improves the physical capacity as well as the quality of life and prolongs the life expectancy to near normal values allowing normal participation in social life.

WO03074119 describes an intravascular flow restrictor comprising a braided tubular structure designed to be placed in the main pulmonary artery for limiting blood pressure in the lungs. The braided structure is designed to be collapsed for placement in a delivery catheter but when ejected from the delivery catheter, assumes a substantially larger diameter disk shaped device having one or more longitudinal channels or passageways therethrough. Adjustment of blood flow is not possible.

EP0647438 describes a reductional stent for reducing a diameter of a duct in a body of a living creature. The stent includes a sleeve-like part having walls provided with perforations, enlarged ends as well as an intermediate area reduced in diameter by a constriction. Thrombogenic threads are provided on an exterior of the sleeve-like part between the enlarged ends. When the stent is in place it is only adjustable by expanding the diameter and thereby increasing the blood flow. Adjustment in order to decrease the blood flow is not possible.

WO10114585 describes a stent made of a bioabsorable, polymer and/or non-polymer material having an elongated body with a proximate end, a distal end, and at least one open channel formed on the exterior surface of the elongated body to provide fluid communication between the proximal end and the distal end. In one embodiment the stent has an elongated centre rod having a proximate end and a distal end and a plurality of leaflets extending outward from the centre rod and forming channels between two neighbouring leaflets to provide fluid communication between the proximal end and the distal end. The diameter of the stent can be reduced by compressing or twisting the channel walls against each other to facilitate implantation. However, once placed at the treatment site the flow cross section cannot be adjusted.

WO03028522 discloses a flow reducing stent. The stent comprising a hollow element adapted for placement in the blood vessel defining a flow passage therethrough. The flow passage comprises at least two sections, one with a larger diameter and one with a smaller diameter, wherein said smaller diameter is smaller than a cross section of the blood vessel. The stent may be provided with an annular inflatable tube around a centre section of the stent. In order to reduce the blood flow the tube is provide with a hose for inflating the tube. Thereby the diameter may be reduced just after positioning the stent in a blood vessel as long as the hose is attached to the tube. However, later adjustment after implantation of the stent and removing of the hose is not possible as the tube cannot be inflated anymore.

U.S. Pat. No. 6,120,534 teaches a flow reducing stent for use in a pulmonary artery to control damage to the lungs in a new born that exhibits multiple, life-threatening cardiopulmonary deformities. The stent comprises a deformable mesh covered with a biocompatible material, the mesh having a conical portion and a constricted region. The stent may be percutaneously and transluminally delivered and deployed in a vessel. The constricted region may then be selectively enlarged employing a conventional dilatation means or device, e.g. a balloon, to adjust the flow impedance created by the constricted region. In an alternative embodiment, the constricted region is preferably formed from a shape-memory material, so that the maximum degree of constriction may be recovered by heating the shape-memory material. However, there is a certain risk of overheating and thereby damaging the surrounding tissue.

WO04014257 describes a flap type flow reducing implant. The flap type reducing implant comprises three flaps that reduce blood flow in a flow passage and/or promote changes in blood stream dynamics depending on the angle of the flaps. The angle of the flaps may be adjusted with a special flap angle adjusting tool. However, the flap type implant is made of a metal tube with its diameter fixed and it cannot be adjusted to a growth in diameter of the blood vessel.

EP1276437 describes a narrowing intraluminal stent comprising hollow body with a flow passage there through. The hollow body has at least one portion of an inner cross sectional dimension smaller than the cross sectional dimension of the lumen, so as to artificially narrow a passage through the body lumen. The stent may have an hourglass or bottleneck shape. When the stent is in place it is only adjustable by expanding the diameter and thereby increasing the blood flow. Adjustment in order to decrease the blood flow is not possible.

Ref 1: Gillum R F. Epidemiology of congenital heart disease in the United States. Am HeartJ 1994;127:919-27.

Ref 2: Hoffman J I, Kaplan S. The incidence of congenital heart disease. J Am Coll Cardiol2002;39: 1890-900.

Ref 3: Marelli A J, Mackie A S, Ionescu-Ittu R, Rahme E, Pilote L. Congenital heart disease in the general population: changing prevalence and age distribution. Circulation 2007; 15:163-72.

Ref 4: Jonas R A. Congenital heart surgery in developing countries. Semin Thorac Cardiovasc Surg Pediatr Card Surg Annu 2008:3-6.

Ref 5: Bernier P L, Stefanescu A, Samoukovic G, Tchervenkov C I. The challenge of congenital heart disease worldwide: epidemiologic and demographic facts. Semin Tho rae Cardiovasc Surg PediatrCard SurgAnnu 2010;13: 26-34.

Ref 6: Neirotti R. Paediatric cardiac surgery in less privileged parts of the world. Cardiol Young 2004;14:341-6.

Ref 7: Yacoub M H. Establishing pediatric cardiovascular services in the developing world: a wake-up call. Circulation 2007;116: 1876-8.

Ref 8: Tchervenkov C I, Jacobs J P, Bernier P L, et al. The improvement of care for paediatric and congenital cardiac disease across the World: a challenge for the World Society for Pediatric and Congenital Heart Surgery. Cardiol Ref 9: Young 2008; 18 Supp12:63-9. Zheleva B. Linked by a common purpose: Global Efforts for Improving Pediatric Heart Health: A Report by Children's Heart Link. Congenital Cardiology Today 2007;5: 1-15.

Ref 10: Mocumbi A O, Lameira E, Yaksh A, Paul L, Ferreira M B, Sidi D. Challenges on the management of congenital heart disease in developing countries. Int J Cardiol 2011; 148:285-8.

Ref 11: Trucco S M, Barnoya], Larrazabal L A, Castaneda A, Teitel D F. Detection rates of congenital heart disease in Guatemala. Cardiol Young 2011; 21:153-60. 23.

Ref 12: Shah G S, Singh M K, Pandey T R, Kalakheti B K, Bhandari G P. Incidence of congenital heart disease in tertiary care hospital. Kathmandu Univ Med J (KUMJ) 2008;6:33-6.

Ref 13: Wickramasinghe P, Lamabadusuriya S P, Narenthiran S. Prospective study of congenital heart disease in children. Ceylon Med J 2001;46:96-8.

Ref 14: Samanek M, Slavik Z, Zborilova B, Hrobonova V, Voriskova M, Skovranek J. Prevalence, treatment, and outcome of heart disease in live-born children: a prospective analysis of 91,823 live-born children. Pediatr Cardiol 1989; 10:205-11.

Ref 15: Saxena A. Congenital heart disease in India: a status report. Indian J Pediatr 2005;72:595-8.

Ref 16: Rao S G. Pediatric cardiac surgery in developing countries. Pediatr Cardiol 2007;28: 144-8.

Ref 17: Guitti J C. Epidemiological characteristics of congenital heart diseases in Londrina, Parana south Brazil. Arq Bras Cardiol 2000;74:395-404.

Ref 18: Penny D J, Vick G W, 3rd. Ventricular septal defect. Lancet 2011;377: 1103-12.

Ref 19: Beghetti M, Galie N. Eisenmenger syndrome a clinical perspective in a new therapeutic era of pulmonary arterial hypertension. J Am Coll Cardiol 2009; 53:733-40.

Ref 20: Pinho P, Von Oppell U O, Brink J, Hewitson J. Pulmonary artery banding: adequacy and long-term outcome. Eur J Cardiothorac Surg 1997; 11: 105-11.

Ref 21: Schranz D, Rupp S, Müller M, et al. Pulmonary artery banding in infants and young children with left ventricular dilated cardiomyopathy: A novel therapeutic strategy before heart transplantation. J Heart Lung Transplant 2013; 32:475-481.

SUMMARY OF THE INVENTION

It is an objective of the invention to provide a stent or a kit of stents for adjustable interventional reduction of blood flow in a blood vessel, with which a reduced blood flow can be easily adjusted by increasing or further reducing the blood flow cross-section through the vessel, even several months or years after implantation of the stent.

This is achieved by a kit of stents according to claim 1 and/or by an adjustable multi-lumen stent according to claim 10.

The kit of stents for adjustable interventional reduction of blood flow in a blood vessel comprises a first reduction stent having in an expanded conformation at least one widened section and a narrowed section, the narrowed section defining a central lumen (herein also called inner or passage lumen) providing fluid communication between an upstream end and a downstream end of the first reduction stent; at least one expandable, e.g. balloon-expandable, dilatation stent having a tubular form with a central lumen and being insertable into and expandable within the central lumen of the first reduction stent in order to enlarge the fluid communication; at least one second reduction stent having a narrowed tubular section with a third central lumen being insertable into the central lumen of the first reduction stent or the central lumen of the dilatation stent in order to reduce the fluid communication, and having anchoring means at its upstream end, the anchoring means having a larger maximal diameter than the narrowed section.

The main part of the kit is the first blood flow reduction stent, which after placement in a blood vessel in its expanded conformation reduces the blood flow through the vessel due to its narrowed section defining an central lumen/passage with a smaller cross-section as compared to the cross-section of the vessel itself. The widened section of the stent is dimensioned to rest against the blood vessel wall. The outer diameter—that is the maximal outer diameter of the widened section—is chosen according to the diameter of the blood vessel an can vary from patient to patient. The inner diameter of the central lumen, i.e. the minimum inner diameter defining the smallest cross-section of the reduction stent, is calculated and chosen according to the reduced blood flow to be achieved by inserting the first reduction stent and also depends on the patient.

In case the blood flow, i.e. the fluid communication, through the central lumen or inner passage of the first reduction stent is too small (i.e. the cross section defined by the inner diameter of the central lumen is too small), a tubular dilatation stent can be placed into the central lumen of the first reduction stent and dilated (e.g. using a balloon) to a desired size in order to correct the blood flow. After placement of the dilatation stent, the flow passage is defined by the central lumen of the dilatation stent having an enlarged diameter as compared to the previously placed first reduction stent thereby increasing the blood flow.

In case the blood flow, i.e. the fluid communication, through the central lumen of the first reduction stent or through the inner lumen of the dilatation stent is too large, the tubular second reduction stent can be placed in the central lumen of the first reduction stent (in case no dilatation stent has been placed) or into the inner lumen of the dilatation stent (in case a dilatation stent has been place and opened to far). With the second reduction stent the blood flow may be further corrected by reducing the blood flow cross-section.

With the dilatation stent and the second reduction stent it is possible to adjust the cross-section of the inner passage in order to obtain the desired reduced blood flow in the blood vessel. If needed, the steps of placing a dilatation stent and/or second reduction stent may be repeated until the desired blood flow is reached. It is also possible to increase or further reduce the blood flow cross-section through the vessel, even several months or years after implantation of the first reduction stent by placing a further dilatation stent or second reduction stent.

Further embodiments of the invention are set forth in the dependent claims.

In some embodiments the kit may have several first and/or second reduction stents each having in an expanded conformation a different inner diameter. Also the outer diameter of the widened section or the anchoring means may be variable. Preferably, all first and/or second reduction stents have the same outer diameter in its maximal expanded conformation.

In some embodiments of the kit the anchoring means may be in the form of an outwardly directed flange or shoulder at a downstream end of the narrowed section of the second reduction stent.

In some embodiments the second reduction stent may have a widened section and the anchoring means define an intermediate section between the narrowed and the widened section of the stent.

The intermediate section is a section of the first or second reduction stent connecting a narrowed section with a widened section. The narrowed an widened sections may be tubular, whereas the intermediate section may have a cone- or funnel-like shape.

In some embodiments of the kit the first reduction stent may have a hourglass, barbell or bottleneck shape and/or the second reduction stent may have a bottleneck shape. In the case that first and second reduction stent have a bottleneck shape the overall shape of the two stent types apart from the chosen diameters is the same. In a kit having several first reduction stent with various inner diameters they may also be used as second reduction stent (i.e. the at least first reduction stent may also be the at least one second reduction stent).

In some embodiments, the dilatation stent may be a conventional tubular stent having in an expanded conformation approximately the same diameter over its entire length. The length may be chosen to the length of the narrowed section of the first reduction stent.

In some embodiments the kit may have several dilatation stent having different maximal outer diameters.

In some embodiments of the kit the at least one first reduction stent and/or the at least one second reduction stent and/or the dilatation stent may be made of a flexible mesh of metal or plastic. The metal may be a self-expandable metal alloy, preferably a nickel-titanium alloy.

At least an intermediate section between the narrowed section and the widened section of the first and/or second reduction stent may be covered with a biocompatible, plastic material, e.g. an expandable polymer sheet, preferable ePTFE, to obtain impermeable walls. Preferably, the cover extends to the regions of the narrowed and widened section which are adjacent to the intermediate section. The cover may extend over the entire widened section and/or the entire narrowed section.

In some embodiments of the kit the narrowed section and the anchoring means of the second reduction stent may be covered with a biocompatible, plastic material.

In some embodiments of the kit the first reduction stent may be a multi-lumen stent having a main body with a proximal end and a distal end, the main body comprising an inner tube-like segment defining the narrowed section with the central lumen and an outer tube-like segment forming the widened section defining an outer lumen of the multi-lumen stent between an inner surface of the outer tube-like segment and an outer surface of the inner tube-like segment. The central lumen is adjustable in diameter and provides fluid communication between the proximal end and the distal end of the multi-lumen stent. The outer lumen is closed at its distal end by a annular cap-like segment defining the intermediate segment connecting the inner tube-like segment with the outer tube-like segment, and being open at the proximal end. The tube-like segment forming the widened section and the tube-like segment forming the narrowed section may have approximately the same length.

In some embodiments the kit may further comprise at least one guide wire and/or at least one dilatation means, e.g. a balloon. Preferably, the dilatation stents of the kit are pre-mounted on the dilatation means.

In each kit the maximal outer diameter of all the first and second reduction stents may be the same and chosen according to the size of the blood vessel of the patient. Each kit may thereby be adapted with the maximal outer diameter to different patient groups (e.g. children, adults).

In some embodiments the kit may further comprise a chart, a table or a spreadsheet in order to determine which inner diameter of the first reduction stent should be chosen for a patient with a given diameter of the blood vessel and a given blood flow rate in order to reach a desired blood flow rate. The given diameter and the given blood flow rate of the patient's blood vessel can be measured. With the chart a suitable first reduction stent with a defined inner diameter of the narrowed section can be easily determined using the measured given values and the value of the desired blood flow rate. It may happen that with the chosen first reduction stent the desired blood flow rate is not reached exactly. In this case the dilatation stent or a second reduction stent may be employed to exactly reach desired blood flow rate.

The medical use of the kit for adjustable interventional reduction of blood flow may be the same as the use of the multi-lumen stent as described below. The kit or the multi-lumen stent may be used to treat Eisenmenger syndrome, pulmonary artery hypertension or left-ventricular cardiomyopathy, or as transjugular intrahepatic portosystemic shunt (TIPS).

The above objective is further achieved by a multi-lumen stent according to claim 10. This stent can be used on itself for adjustable interventional reduction of blood flow in a blood vessel or as a part of the kit described above.

The multi-lumen stent for interventional reduction of blood flow in a blood vessel has a main body with a proximal end and a distal end. The main body comprises an inner tube-like segment defining a central lumen (herein also called inner or passage lumen) of the multi-lumen stent and an outer tube-like segment defining an outer lumen of the multi-lumen stent between an inner surface of the outer tube-like segment and an outer surface of the inner tube-like segment. The central lumen is adjustable in diameter and provides fluid communication between the proximal end and the distal end of the multi-lumen stent. The outer lumen is closed at its distal end by a annular cap-like segment connecting the inner tube-like segment with the outer tube-like segment, and is open at the proximal end allowing the introduction of dilatation means. The cap-like segment is flexible and preferably has a rounded shape in order to adjust to a changing cross-section of the central lumen.

Adjustable in the context of the present invention means that the flow cross-section of the multi-lumen stent can be increased or decreased even when it is placed inside a blood vessel and at any time after placement of the adjustable multi-lumen stent inside a blood vessel.

When implanting the adjustable multi-lumen stent the outer tube-like segment abuts to the inner surface of a blood vessel. The blood flow—directed from the proximal end towards the distal end—is then reduced to a predefined flow due to a reduction of the flow cross-section of blood vessel to the flow cross-section defined by the central or inner lumen (also called passage lumen). After placing the multi-lumen stent at the desired position in the blood vessel, it may have a predefined flow cross-section resulting in a certain blood flow. In order to increase the blood flow relative to the predefined flow, an appropriate dilatation means or instrument, e.g. a balloon, may be placed inside the central lumen to expand the flow cross-section of the inner lumen.

The dilatation means or instrument may already be part of the instrumentation for placing the adjustable multi-lumen stent inside a blood vessel. Often it may be necessary to further decrease the blood flow or to reduce the flow cross-section relative to the predefined state right after placement. In order to decrease the blood flow, an appropriate dilatation means or instrument, e.g.

one or more balloons, may be placed in the outer lumen surrounding the central lumen. Expanding the cross-section of the outer lumen leads to a reduction of the cross-section of the inner lumen because the diameter of the outer tube-like segment of the stent abuts against the inner surface of the blood vessel and is thereby stabilized. Reduction of the cross-section of the inner lumen results in a reduction of blood flow through the multi-lumen stent. Ideally, several balloons may be inserted in the outer lumen in a regularly spaced manner to evenly decrease the diameter of the central lumen.

In order to help adjusting the flow cross-section of the multi-lumen stent to the desired blood flow, pressure measurement distal and proximal of the multi-lumen stent are possible. This allows a direct measurement of the pressure gradient over adjustable the multi-lumen stent.

Because the central lumen and the outer lumen remain open at their proximal end, even after implantation of the adjustable multi-lumen stent, its central and outer lumen will still be accessible for suitable dilatation means in order to adjust the blood flow—that is the flow cross-section of the central lumen—to changing conditions of the patient.

The multi-stent is suitable for reduction of blood flow in a fully adjustable manner, meaning that the blood flow can be increased or decreased even after implantation of the stent. The adjustable multi-lumen stent may be used for the reduction of pulmonary artery blood flow in patients to avoid the development of pulmonary artery hypertension and in patients with pulmonary hypertension and established Eisenmenger's syndrome associated with uncorrected heart disease. The adjustable multi-lumen stent is further suitable to reduce pulmonary blood flow in patients with left ventricular dilated cardiomyopathy.

Further embodiments of the invention are set forth in the dependent claims.

In some embodiments the inner tube-like segment may be arranged concentrically inside the outer tube-like segment.

In some embodiments the main body or at least one of the segments of the main body, that is the inner tube-like segment, the outer tube-like segment or and the cap-like segment, is made of a material with superelastic properties (also called pseudoelasticity). Such material also has a shape-memory effect. The material may be metal or plastic. Preferably, it is a metal alloy with superelastic properties, more preferably nitinol. An adjustable multi-lumen stent made of material with superelastic properties may be introduced in a crimped/compressed manner via a catheter into the blood vessel. When released from a catheter at the desired position the adjustable multi-lumen stent expands to its predefined size. Such a stent is also called self-expandable. Advantageously, the predefined size of the outer tube-like segment is chosen larger than actually required by the diameter of the target blood vessel, such that an adjustable multi-lumen stent, implanted into a still growing patient, automatically adjusts itself to the increasing diameter of the blood vessel.

In some embodiments the main body may comprise one covered tubular meshed stent folded back over itself at the distal end thereby forming the inner tube-like segment, the outer tube-like segment and the cap-like segment. The segment where the stent is folded defines the cap-like segment. All segments may be covered with an expandable plastic cover.

In some embodiments the main body may comprise two tubular meshed stents arranged within each other thereby forming the inner tube-like segment and the outer tube-like segment. The segments may be covered by an expandable plastic cover, which may also form the cap-like segment at the distal end of the adjustable multi-lumen stent.

In some embodiments the main body or at least one segment of the main body is/are made of flexible mesh of metal or plastic covered with an expandable polymer sheet, preferably ePTFE, to obtain impermeable segment walls. It is understood that the three segments of the main body should be impermeable to blood in order to fulfil the desired function of interventional reduction of blood flow, due to reduction of the flow cross-section. However, in all embodiments some orifices may exist in order to prevent coagulation of blood in the outer lumen as described further below.

In some embodiments the main body of the adjustable multi-lumen stent may comprise two conventional meshed stents with different diameter defining the inner and outer tube-like segment of the main body. The stent of the outer tube-like segment and optionally the stent of the inner tube-like segment may be of self-expanding material as described above. The two stents are covered with an expandable polymer sheet to obtain impermeable stent walls. At the same time the expandable sheet, which is folded back over itself defines the cap-like segment of the main body. The two meshed stents may be positionally stabilized to each other by stabilization means e.g. connecting elements or wires at the distal end of the main body connecting the inner tube-like segment with the outer tube-like segment in the region of the cap-like segment. Additional connecting elements or connecting wires acting as stabilization means may be provided at the proximal end of the main body.

As described previously the overall main blood flow is defined by the diameter or cross-section of the central lumen. However, in some embodiments the annular cap-like segment of the main body may be provided with at least one orifice, preferably three orifices, to reduce the risk of coagulation of blood in the outer lumen, by allowing a little blood flow through the outer lumen. The orifices in the cap-like segment are held small such that just enough blood flows in order to prevent coagulation in the outer lumen, which would otherwise lead to a considerable health risk and impair later adjustment of the blood flow through the adjustable multi-lumen stent. The same orifices may also be used as a guide for correctly placing the dilatation means in the outer lumen via a guide wire. Therefore, the at least two orifices, preferably three orifices, may be arranged in a regular pattern around the central axis of the main body. The orifices may also be arranged at the distal end of the inner tube-like segment fluidly connecting the distal end of the outer lumen with the distal end of the inner lumen.

In some embodiments the adjustable multi-lumen stent may further comprise at least two outer tubular stents, preferably three outer tubular stents, arranged in the outer lumen of the main body in a regular pattern around the central axis of the main body. Again, the orifices described beforehand may be used to guide placement of the outer tubular stents by pushing the guide wire into the orifice. The outer tubular stents facilitate regular placement of the dilatation means in the outer lumen to decrease the diameter/cross-section of the central lumen. They further act as stabilization means to stabilize the inner lumen centrally inside the outer tube-like segment defining the outer wall of the outer lumen.

In some embodiments the adjustable multi-lumen stent may further comprise an inner tubular stent arranged in the inner lumen of the main body. The tubular stent may be a conventional expandable stent.

The outer and/or the inner tubular stents may be desirable in case the inner tube-like segment is made of a material with superelastic properties (shape memory effect), in order to provide the required force to adjust the inner lumen to the desired cross-section. Otherwise the inner tube-like segment may move back to its memorized shape or size after removal of the respective dilatation means. However, when the inner tube-like segment does not have superelastic properties (shape memory effect), the inner stent or even the outer stent may be omitted.

When placing the adjustable multi-lumen stent into a blood vessel of a patient, the main body is in a crimped or compressed state inside a catheter in order to direct it to the desired position. When released from the catheter the main body expands to the desired size and the outer tube-like segment abuts the inner surface of the blood vessel. As a next step an optional inner stent and/or one or more outer stents may be placed in the inner or outer lumen respectively and the cross-section of the central lumen is adjusted to the desired size by respective dilatation means introduced into the central lumen or the inner stent (increasing blood flow) or into the outer lumen or the outer stents (decreasing blood flow).

The invention further covers a kit of parts comprising an adjustable multi-lumen stent with the main body as described above and at least one guide wire and at least one dilatation means for placing and adjusting the multi-lumen stent. The kit may further comprise several conventional tubular stents for placement in the inner and/or outer lumen of the main body.

The adjustable multi-lumen stent may be used in medical indications where a reduction of blood flow is desired, such as but not limited to the medical indications described above. Recently pulmonary artery banding in infants and young children with left ventricular dilated cardiomyopathy has been described (Ref 21). Also for this medical indication the adjustable multi-lumen stent is suitable to reduce blood flow.

It is understood that the multi-lumen stent can be regarded as an invention by itself independent of the kit of parts, which includes first and second reduction stent and dilatation stent.

BRIEF EXPLANATION OF THE FIGURES

The invention is described in greater detail below with reference to embodiments that are illustrated in the figures. The figures show:

FIG. 7 a perspective view onto the proximal end of the main body of an adjustable multi-lumen stent with a covered mesh;

FIG. 8 a perspective view onto the distal end of the main body of an adjustable multi-lumen stent with a covered mesh;

FIG. 9 an exploded view of the main body of an adjustable multi-lumen stent with two meshed stents and a plastic cover;

EMBODIMENTS OF THE INVENTION

Figure 1:
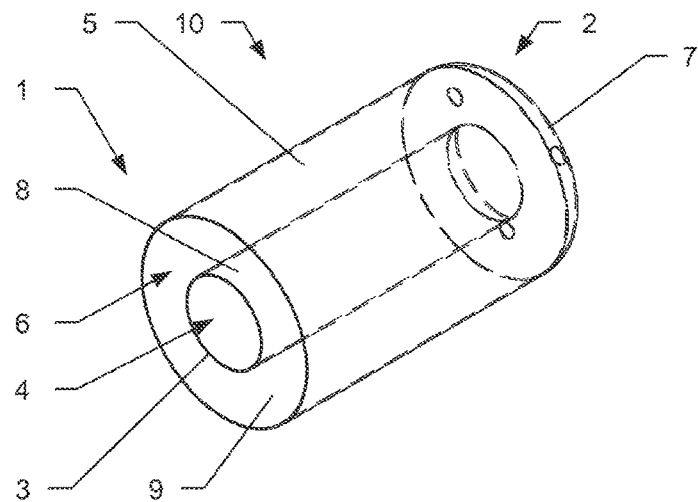
FIG. 1 a perspective view onto the proximal end of the main body of an adjustable multi-lumen stent.
Figure 2:
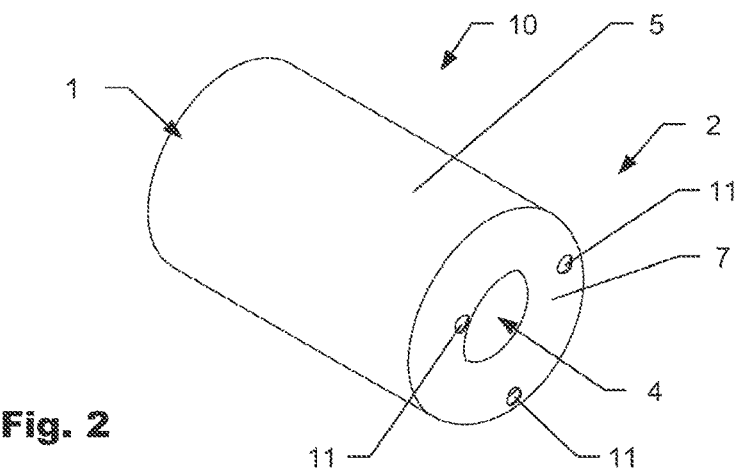
FIG. 2 a perspective view onto the distal end of the main body of an adjustable multi-lumen stent.

FIG. 1 and FIG. 2 each show a perspective view of an adjustable multi-lumen stent for interventional reduction of blood flow in a blood vessel (hidden lines are shown as dashed lines). The adjustable multi-lumen stent comprises a main body 10 with a proximal end 1 and a distal end 2. The main body 10 comprises a inner tube-like segment 3 defining a central lumen 4 (also called passage lumen), which provides fluid communication between the proximal end 1 and the distal end 2. The main body 10 further comprises an outer tube-like segment 5 defining an outer lumen 6 (also called blocked lumen). The outer lumen 6 is situated between an inner surface 9 of the outer tube-like segment 5 and an outer surface 8 of the inner tube-like segment 3. At the distal end 2 the outer lumen 6 is closed by a cap-like segment 7 of the main body 10. In order to prevent coagulation of blood in the outer lumen 6, the cap-like segment 7 or the distal end of the inner tube-like segment may be provided with orifices 11 to allow a little blood flow through the outer lumen.

In the shown embodiment the cap-like segment has three orifices 11 regularly spaced apart around the central axis of the main body 10.

In the implanted state the blood flows in direction from the proximal end 1 to the distal end 2 only through the central or passage lumen 4 of the main body 10 (apart from the very little flow through the outer lumen to avoid coagulation) and thereby reduced the flow cross section of the blood vessel. In order to increase the blood flow, the cross section/diameter of the inner lumen 4 may be expanded by inserting an appropriate dilatation means, e.g. a balloon, into the central lumen 4. In order to reduce the blood flow, the cross section/diameter of the inner lumen 4 may be reduced by inserting one or more appropriate dilatation means or devices, e.g. a balloons, into the outer lumen 6. The orifices 11 in the cap-like segment may be used as guiding holes for placing the guide wire of the dilatation means. The multi-lumen stent with such inner and outer lumen 6 is adjustable in both direction even after implantation.

Figure 3:
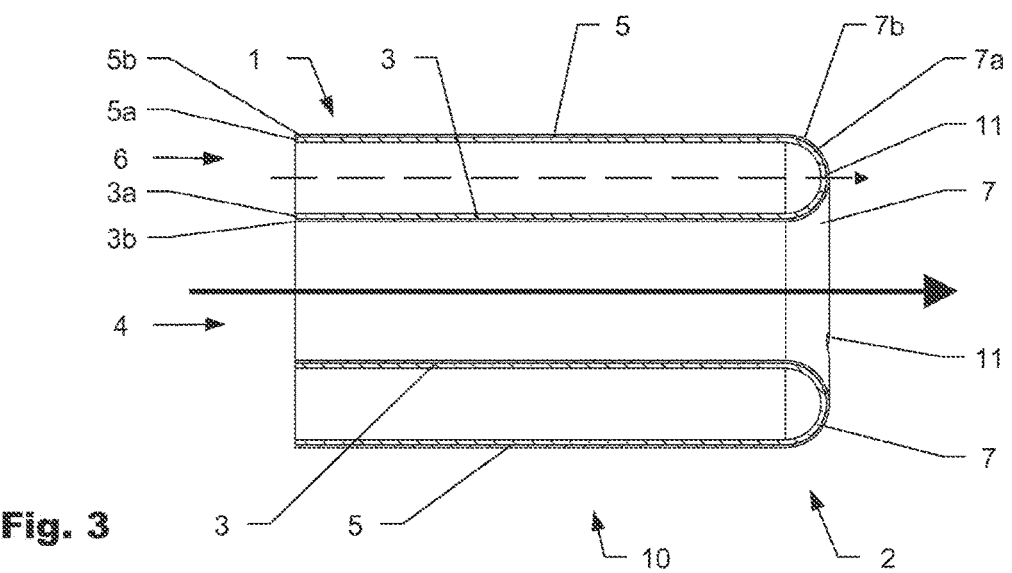
FIG. 3 a cross section through the main body of an adjustable multi-lumen stent.

FIG. 3 show a cross sectional view of the main body 10 of an adjustable multi-lumen stent with an inner tube-like segment 3 forming the central lumen 4 and an outer tube-like segment 5 forming the outer lumen 6. The outer lumen 6 is closed at its distal end 2 with a rounded cap-like segment 7. The main blood flow leads through the central lumen 4 (thick arrow in FIG. 3) and is reduced to the flow cross-section of the central lumen 4. The cap-like segment is provided with at least one orifice 11 to reduce the risk of coagulation of blood in the outer lumen 6, by allowing a little blood flow through the outer lumen (thin dashed arrow in FIG. 3). In the embodiment shown in FIG. 3 the main body 10 comprises a meshed structure 3a, 5a, 7a covered by an expandable plastic cover 3b, 5b, 7b. The meshed structure of the main body 10 may be manufactured from one tube-like mesh folded back over itself.

Figure 4:
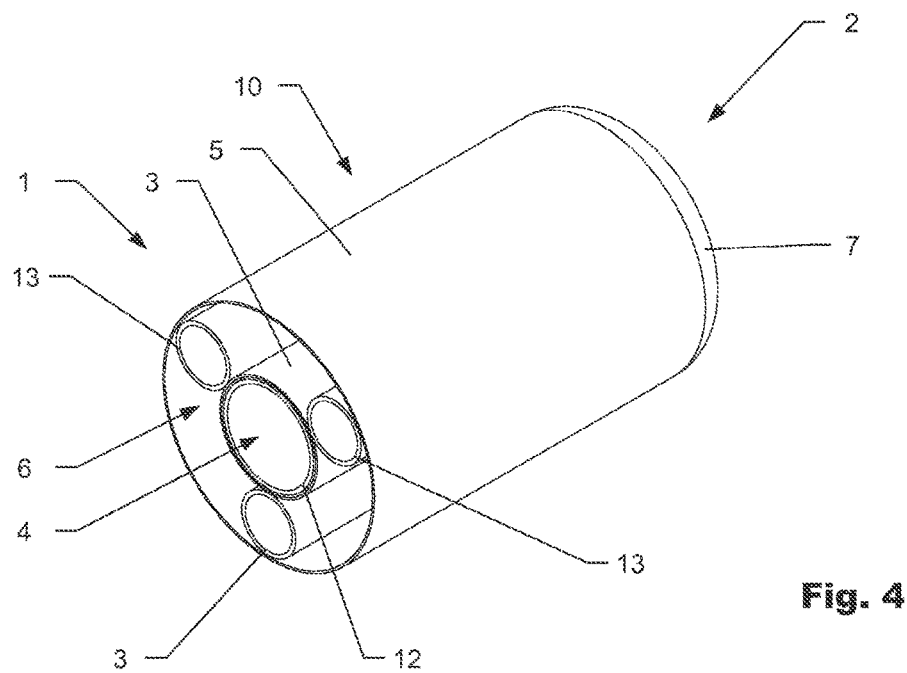
FIG. 4 a perspective view of the adjustable multi-lumen stent.

FIG. 4 shows a perspective view of an embodiment of an adjustable multi-lumen stent comprising an additional inner stent 12 and three additional outer stents 13. The inner stent 12 is arranged inside the inner lumen 4 to stabilize the inner flow cross-section of the adjustable multi-lumen stent. The outer stents 13 are arranged in the outer lumen 6 in a regular pattern (spaced apart by 120 degrees) around the inner lumen 4. The outer stents 13 stabilize the inner lumen 4 concentrically within the outer lumen 6 and are used to decrease the flow cross-section of the inner lumen 4 by suitable dilatation means as described above. Both the inner stent 12 and the outer stents 13 reach from the proximal end 1 of the adjustable multi-lumen stent to its distal end 2.

Figure 5A:
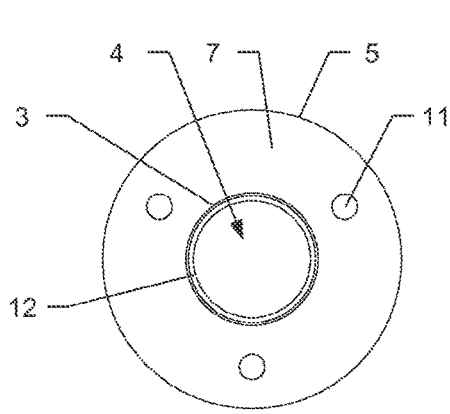
FIG. 5 a plan view onto the proximal end (a) and the distal end (b) of the adjustable multi lumen stent.
Figure 5B:
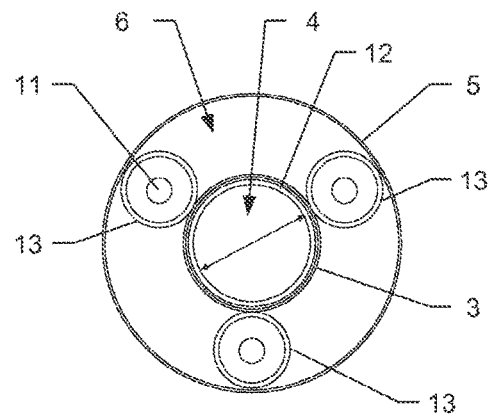
Figure 6A:
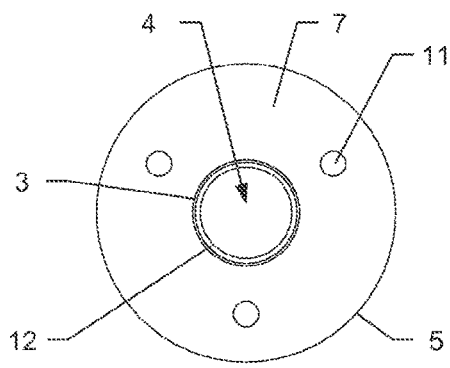
FIG. 6 a plan view onto the proximal end (a) and the distal end (b) of the adjustable multi-lumen stent with reduced flow cross-sections.
Figure 6B:
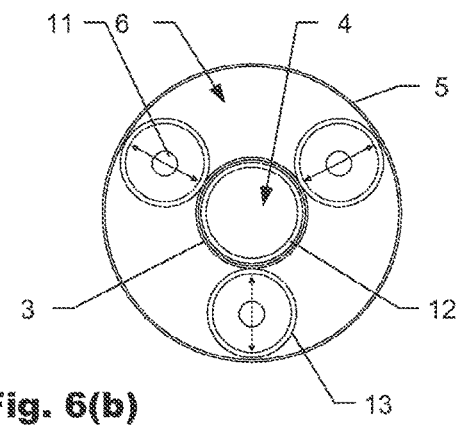

FIG. 5 and FIG. 6 show plan views onto the proximal end (FIG. 5(a) and FIG. 6(a)) and the distal end (FIG. 5(b) and FIG. 6(b)) of the multi lumen stent of FIG. 4. The adjustable multi-lumen stent of FIG. 6 has a reduced flow cross-section relative to the flow cross-section in FIG. 5.

FIG. 5(a) and FIG. 6(a) show the distal end of the adjustable multi-lumen stent with the cap-like segment 7 closing the outer lumen. The distal opening of the inner lumen 4 is centrally arranged along the axis of the adjustable multi-lumen stent. The orifices 11 in the cap-like segment 7 are evenly arranged around the axis of the adjustable multi-lumen stent.

FIG. 5(b) and FIG. 6(b) show the proximal end of the adjustable multi-lumen stent with the open inner lumen 4 and the open outer lumen 6. The outer lumen 6 accommodates the three outer stents 13 evenly arranged around the inner lumen 4 or the inner stent 12 and aligned with the orifices 11. Even dilatation of the three outer stents 13 (arrows in FIG. 6(b)) leads to a decrease of the diameter or cross-section of the inner stent 12 (see FIG. 6(a) and FIG. 6(b)). Reversely, dilatation of the inner stent 12 (arrows in FIG. 6(a)) leads to decrease of the cross-section of the outer lumen 6. The flexible or rounded cap-like segment 7 adjusts to the various cross-sections of the inner lumen 4.

FIG. 7 shows a perspective view onto the proximal end 1 of the main body 10 of an adjustable multi-lumen stent with a covered mesh. FIG. 8 shows a perspective view onto the distal end of the main body of FIG. 7. The outer tube-like segment 5 comprises a tube-like mesh 5a covered with an expandable plastic cover 5b. The inner tube-like segment comprises a tube-like mesh 3a covered with an expandable plastic cover 3b. The two tube-like meshes 3a, 5a may be individual conventional meshed stents with different diameter arranged concentrically within each other (as shown in FIG. 9). In the shown embodiment the cover 3b, 5b may be a single plastic sheet folded back over itself to form a cap-like segment 7 at the distal end of the main body 10. FIG. 9 shows an exploded view of the main body 10 of an adjustable multi-lumen stent comprising two meshed stents 3a, 5a and a plastic cover forming the impermeable outer an inner wall (5a, 5b) of the respective tube-like segments and the cap-like segment 7. The cover in the region of the cap-like segment is provided with the above described orifices 11.

The meshed structure of the main body 10 may also be manufactured from one tube-like mesh folded back over itself. In that case the plastic cover would cover the inner surface of the inner tube-like segment.

Figure 10:
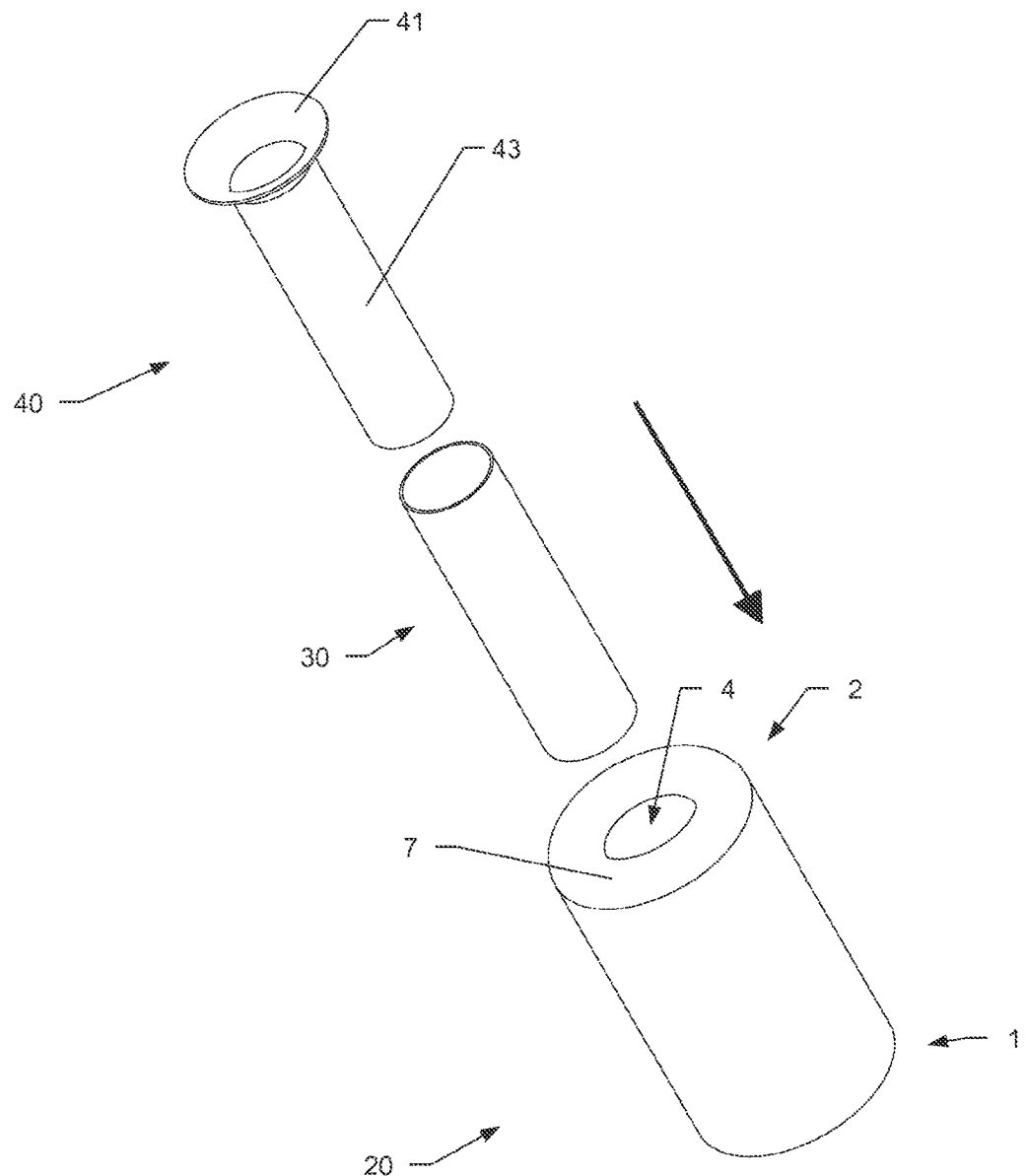
FIG. 10 a first reduction stent, a dilatation stent and a second reduction stent as parts of a kit.
Figure 11A:
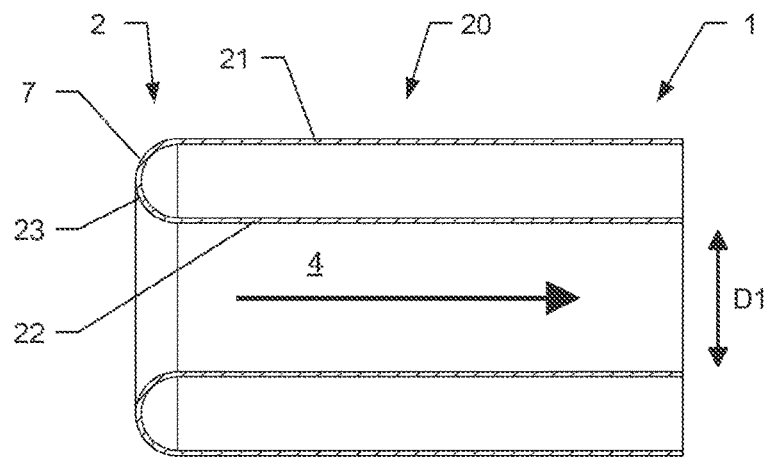
FIG. 11 a cross-sectional view of different steps (a)-(c) using the stents of FIG. 10.
Figure 11B:
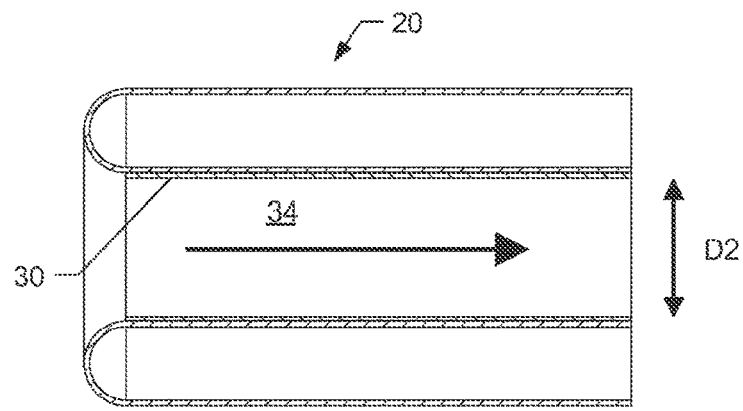

FIG. 10 and FIG. 11 show an alternative way for adjustable interventional reduction of blood flow in a blood vessel. FIG. 10 shows three different stent types as parts of a kit for performing this alternative way and FIG. 11 shows under (a) to (c) three general steps for adjusting the blood flow by changing the cross-section for fluid communication through the stent(s) using such a kit.

The main part of the kit as shown in FIG. 10 is a first blood flow reduction stent 20 in the form of the multi-lumen stent as described before in its simplest version. The first reduction stent 20 has a main body with a proximal end 1 and a distal end 2. The main body comprises an inner tube-like segment (narrowed section 22) defining a central lumen 4 of the first reduction stent 20 and an outer tube-like segment (widened section 21) defining an outer lumen of the first reduction stent 20 located between an inner surface of the outer tube-like segment and an outer surface of the inner tube-like segment. Both segments have approximately the same length. The central/inner lumen 4 provides fluid communication between the proximal end and the distal end. The outer lumen is closed at its distal end 2 by an annular cap-like segment 7 (intermediate section 23) connecting the inner tube-like segment with the outer tube-like segment. The main structure of the first reduction stent 20 may be a mesh of self-expandable nitinol (a nickel-titanium alloy showing a shape memory effect) with a predefined outer diameter and inner diameter D1. The outer diameter is chosen according to the diameter of the blood vessel. The inner diameter is calculated and chosen according to the reduced blood flow to be achieved by placing the first reduction stent 20 into a blood vessel of the patient.

The first reduction stent 20 may be placed inside a blood vessel (not shown) to reduce the blood flow there through. Opposite to the placement as described beforehand, in the alternative way for interventional reduction of blood flow the distal end 2 of the first reduction stent is pointing upstream and the proximal end 1 is pointing downstream. The thick arrow in FIG. 10 and FIG. 11 shows the direction of the blood stream.

The kit further comprises at least one tubular dilatation stent 30 and at least one second reduction stent 40. The kit may have several of each type of stent of various size regarding their length and outer and/or inner diameter.

After placement of the first reduction stent 20 into a blood vessel the distal end having the cap-like segment 7 is pointing upstream. The self-expandable first reduction stent 20 has a predefined inner diameter D1, chosen according to the situation of the patient and the calculated interventional reduction of blood flow needed for treatment.

In case the blood flow through the inner/passage lumen 4 of the first reduction stent 20 is too small (i.e. the cross section defined by the inner diameter D1 of the inner lumen is too small), the tubular dilatation stent 30 can be placed into the inner lumen 4 of the first reduction stent 20 and dilated to a desired size in order to increase fluid communication. The dilatation stent 30 may be a conventional expandable bare-metal stent without a cover, which can be expanded with a balloon in order to open the inner lumen 4 of the first reduction stent 20. After placement, the flow passage is defined by the inner lumen 34 of the dilatation stent 30 having an enlarged diameter D2 with respect to the previous diameter D1 allowing a larger blood flow (FIG. 11(b)). The dilatation stent 30 may be in the form of an expandable mesh.

Figure 11C:
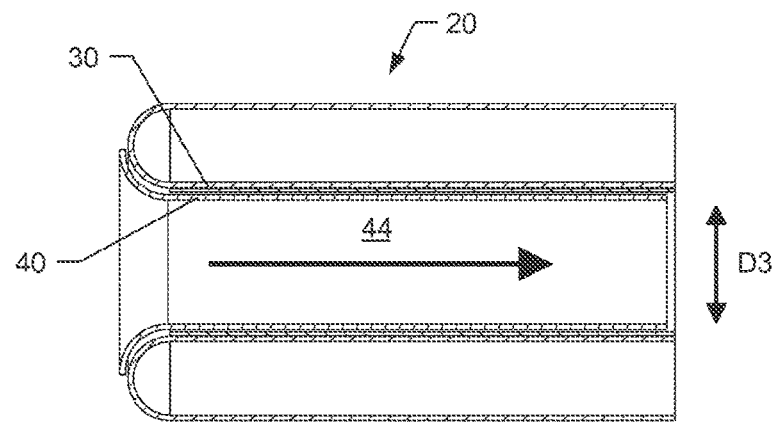

In case the blood flow through the inner lumen 4 of the first reduction stent 20 is too large (i.e. the cross section defined by the inner diameter D1 or D2 of the inner lumen 4 or 34 is too large), the second reduction stent 40 can be placed in the inner lumen 4 of the first reduction stent 20 (in case no dilatation stent has been placed) or into the inner lumen 34 of the dilatation stent 30 (in case a dilatation stent has been place and opened to far) in order to decrease fluid communication. The second reduction stent 40 may also be self-expandable and has an inner lumen 44 with predefined inner diameter D3. The kit may therefore have several second reduction stents with different inner diameters D3. By placing the second reduction stent 40 the blood flow (i.e. fluid communication) is further reduced. FIG. 11(c) shows a second reduction stent 40 placed inside a dilatation stent 30. In the embodiment shown in FIGS. 10 and 11(c) the second reduction stent 40 has anchoring means 41 at least at its downstream end in the form of an outwardly bent flange or widened anchoring segment. The outer diameter of the flange or anchoring segment is chosen smaller than the diameter of the blood vessel but larger than the inner diameter D1 of the first reduction stent 20 after placement or the inner diameter D2 of the dilatation stent 30 after placement.

If needed, the steps of placing a dilatation stent 30 and/or second reduction stent 40 may be repeated until the desired blood flow is reached.

Figure 12A:
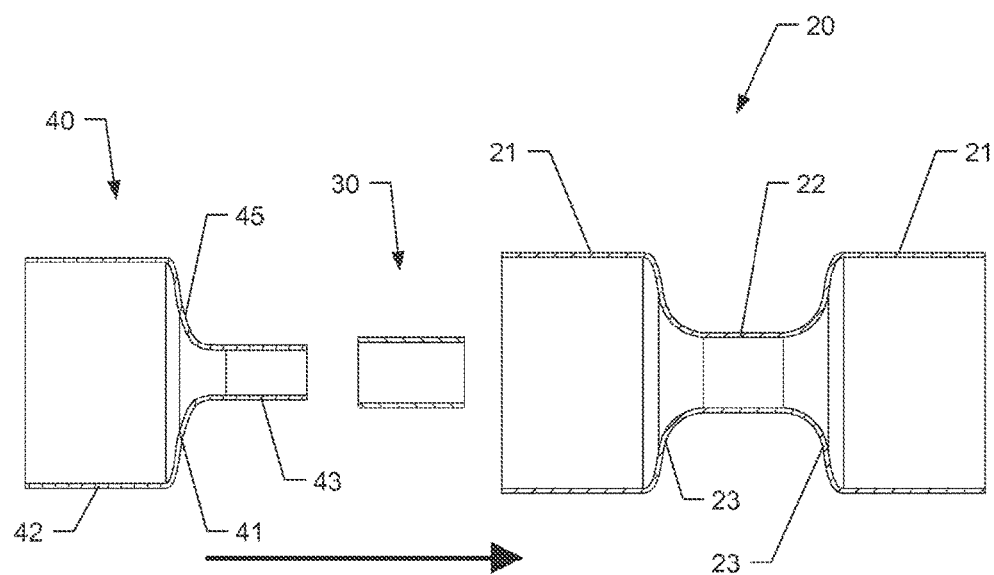
FIG. 12 a first reduction stent, a dilatation stent and a second reduction stent as parts of a kit, under (a) in an exploded view and under (b) placed within each other.
Figure 12B:
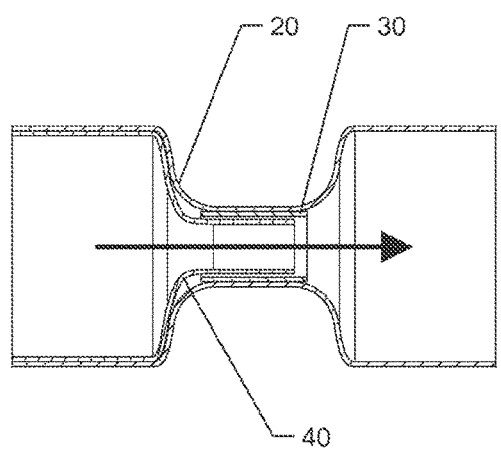

The stents of the kit may also have different shapes e.g. as shown in FIG. 12. Here, the first blood flow reduction stent 20 has an hour-glass or barbell shape with two widened sections 21 on each side of a narrowed section 22. The narrowed section defines the inner lumen 24 of the first reduction stent 20. Again, the first reduction stent may be a self-expandable mesh. At least the an intermediate sections 23 between the narrowed and widened section narrowed, and preferable the adjacent regions thereto, may be covered to restrict blood flow through the mesh.

The second reduction stent 40 is in the form of a bottleneck with a widened section 42 followed by a narrowed section 43 at its downstream end. The narrowed section 43 forms the inner lumen 44 of the second reduction stent 40. The second reduction stent 40 may be a self-expandable mesh e.g. of Nitinol (nickel-titanium alloy). At least the narrowed section 43 and an intermediate section 45 between the narrowed and widened section may be covered to restrict blood flow through the mesh. The intermediate section 45 also provides the anchoring means 41 in order to hold the second reduction stent 40 in place.

The first reduction stent may also have a bottleneck shape like the second reduction stent (not shown). In this case first and second reduction stents provided in a kit may be the same. The kit has then only one type of reduction stent with different inner diameters that may be used in the way of the first and second reduction stents.

The three different stent types of FIG. 12 may be employed in the same way as described with respect to FIG. 11.

In all embodiments of the kit, at least the narrowed section 22, 43 and an intermediate section 23, 45 (or anchoring means 41) between the narrowed section 22, 43 and the widened section 21, 42 of the first and/or second reduction stent 20, 40 may be covered with a biocompatible, plastic material, e.g. an expandable polymer sheet, preferable ePTFE, to obtain impermeable walls.

It is understood, that the kit of stents comprising a first reduction stent, at least one dilatation stent and at least one second reduction stent may be regarded as a separate invention as well as the multi-lumen stent described beforehand may be seen as a separate invention.

REFERENCE SIGNS 1 proximal end
1' downstream end
2 distal end
2' upstream end
3 inner tube-like segment
3a meshed inner tube-like segement
3b cover
4 inner lumen/central lumen/passage lumen
5 outer tube-like segment
5a meshed outer tube-like segement
5b cover
6 outer lumen/blocked lumen
7 cap-like segment
7a meshed cap-like segment
7b cover
8 inner surface
9 outer surface
10 main body
11 orifice
12 inner stent
13 outer stent
20 first reduction stent
21 widened section
22 narrowed section
23 intermediate section
24 central lumen/inner lumen/passage lumen
30 dilatation stent
34 inner lumen
40 second reduction stent
41 anchoring means
42 widened section
43 narrowed section
44 central lumen/inner lumen/passage lumen
45 intermediate section

The invention claimed is:

1. A kit of stents for adjustable interventional reduction of blood flow in a blood vessel, the kit comprising:
    a first reduction stent having in an expanded conformation at least one widened section and a narrowed section, the narrowed section defining a central lumen providing fluid communication between an upstream end and a downstream end of the first reduction stent;
    at least one expandable dilatation stent having a tubular form with a second central lumen and being insertable into and expandable within the central lumen of the first reduction stent to increase fluid communication;
    at least one second reduction stent having a narrowed tubular section with a third central lumen being insertable into the central lumen of the first reduction stent or the central lumen of the dilatation stent to decrease fluid communication, and having anchoring means at an upstream end, the anchoring means having a larger maximal diameter than the narrowed section,
    wherein the dilation stent is insertable into the central lumen of the first reduction stent and provides fluid communication between the upstream and downstream ends of the first reduction stent and the second reduction stent is insertable into the central lumen of the first reduction stent and provides fluid communication between the upstream and downstream ends of the first reduction stent.

2. The kit according to claim 1, wherein the kit comprises several first and/or second reduction stents each having in an expanded conformation a different inner diameter.

3. A kit of stents for adjustable interventional reduction of blood flow in a blood vessel, the kit comprising:
    a first reduction stent having in an expanded conformation at least one widened section and a narrowed section, the narrowed section defining a central lumen providing fluid communication between an upstream end and a downstream end of the first reduction stent;
    an expandable dilatation stent having a tubular form with a second central lumen and being insertable into and expandable within the central lumen of the first reduction stent to enlarge the fluid communication;
    a second reduction stent having a narrowed tubular section with a third central lumen being insertable into the central lumen of the first reduction stent or the central lumen of the dilatation stent to reduce the fluid communication, and having anchoring means at an upstream end, the anchoring means having a larger maximal diameter than the narrowed section,
    wherein the anchoring means is in the form of an outwardly directed flange or shoulder at a downstream end of the narrowed section of the second reduction stent or the anchoring means define an intermediate section between a widened section at the upstream end of the second reduction stent and the narrowed section of the second reduction stent.

4. The kit according to claim 1, wherein the first reduction stent has an hourglass, barbell or bottleneck shape.

5. The kit according to claim 1, wherein the second reduction stent has a bottleneck shape.

6. The kit according to claim 1, wherein the one first and/or the at least one second reduction stent and/or the dilatation stent are made of a flexible mesh of metal or plastic.

7. The kit according to claim 6, wherein the metal is a self-expandable metal alloy, preferably a nickel-titanium alloy.

8. The kit according to claim 1, wherein at least an intermediate section between the narrowed section and the widened section of the first and/or second reduction stent are covered with a biocompatible, plastic material.

9. The kit according to claim 1, wherein the first reduction stent is a multi-lumen stent having a main body with a proximal end and a distal end, the main body comprising an inner tube-like segment defining the narrowed section with the central lumen and an outer tube-like segment forming the widened section defining an outer lumen of the multi-lumen stent between an inner surface of the outer tube-like segment and an outer surface of the inner tube-like segment; the central lumen being adjustable in diameter and providing fluid communication between the proximal end and the distal end of the multi-lumen stent; the outer lumen being closed at a distal end by an annular cap-like segment defining the intermediate segment connecting the inner tube-like segment with the outer tube-like segment, and being open at a proximal end.

10. An adjustable multi-lumen stent for interventional reduction of blood flow in a blood vessel, the multi-lumen stent having a main body with a proximal end and a distal end, the main body comprising an inner tube-like segment defining a central lumen of the multi-lumen stent and an outer tube-like segment defining an outer lumen of the multi-lumen stent between an inner surface of the outer tube-like segment and an outer surface of the inner tube-like segment;
the central lumen being adjustable in diameter and providing fluid communication between the proximal end and the distal end of the multi-lumen stent;
the outer lumen being closed at a distal end by an annular cap-like segment connecting the inner tube-like segment with the outer tube-like segment, and being open at a proximal end allowing the introduction of a dilator from the open proximal end of the outer lumen to the closed distal end of the outer lumen.

11. The multi-lumen stent according to claim 10, wherein the inner tube-like segment is arranged concentrically inside the outer tube-like segment.

12. The multi-lumen stent according to claim 10, wherein the main body or at least one of the segments of the main body is made of a material with superelastic properties.

13. The multi-lumen stent according to claim 10, wherein the main body or at least one of the segments of the main body is/are made of a flexible tube-like mesh of metal or plastic covered with an expandable polymer sheet, to provide impermeable segment walls.

14. An adjustable multi-lumen stent for interventional reduction of blood flow in a blood vessel, the multi-lumen stent having a main body with a proximal end and a distal end, the main body comprising an inner tube-like segment defining a central lumen of the multi-lumen stent and an outer tube-like segment defining an outer lumen of the multi-lumen stent between an inner surface of the outer tube-like segment and an outer surface of the inner tube-like segment
the central lumen being adjustable in diameter and providing fluid communication between the proximal end and the distal end of the multi-lumen stent,
the outer lumen being closed at a distal end by an annular cap-like segment connecting the inner tube-like segment with the outer tube-like segment, and being open at a proximal end allowing the introduction of a dilator, wherein the annular cap-like segment of the main body is provided with at least two orifices.

15. The multi-lumen stent according to claim 14, wherein the at least two orifices are arranged in a regular pattern around the central axis of the main body.

16. The multi-lumen stent according to claim 10, wherein the main body comprises one covered tubular meshed stent folded back over itself at the distal end thereby forming the inner tube-like segment, the outer tube-like segment and the cap-like segment.

17. The multi-lumen stent according to claim 10, wherein the main body comprises two tubular meshed stents arranged within each other and covered with an expandable plastic cover, the cover forming the cap-like segment.

18. The multi-lumen stent according to claim 10, wherein the multi-lumen stent further comprises at least two outer tubular stents arranged in the outer lumen of the main body in a regular pattern around the central axis of the main body.

19. The multi-lumen stent according to claim 10, wherein the multi-lumen stent further comprises an inner tubular stent arranged in the central lumen of the main body.

20. The multi-lumen stent according to claim 12, wherein the main body or at least one of the segments of the main body is made of a metal alloy with superelastic properties, preferably nitinol.

* * * * *